United States Patent [19]

Löhner et al.

[11] Patent Number: 5,173,304

[45] Date of Patent: Dec. 22, 1992

[54] AGENTS FOR THE TREATMENT OF SEVERE PAIN AND PREPARATION OF SAID AGENTS

[75] Inventors: Manfred Löhner; Klaus Posselt, both of Bonn; Ute Vogtle-Junkert, Alfter; Hans H. Wagener, Meckenheim, all of Fed. Rep. of Germany

[73] Assignee: Dolorgiet Beteiligungs GmbH, St. Augustin, Fed. Rep. of Germany

[21] Appl. No.: 567,358

[22] Filed: Aug. 14, 1990

[30] Foreign Application Priority Data

Aug. 17, 1989 [DE] Fed. Rep. of Germany ....... 3927113

[51] Int. Cl.5 ............................................. A61K 9/64
[52] U.S. Cl. ................................. 424/456; 424/458; 424/451
[58] Field of Search ................................ 424/451, 465

[56] References Cited

U.S. PATENT DOCUMENTS 4,571,400 2/1986 Arnold ................................. 514/282
4,839,176 6/1989 Pankhania et al. ................. 424/465
4,844,907 7/1989 Elger et al. .......................... 424/465
4,894,234 1/1990 Sharma et al. ...................... 424/441
4,923,898 5/1990 Sunshine et al. .................... 514/557

FOREIGN PATENT DOCUMENTS

WO8504589 10/1985 PCT Int'l Appl. .

Primary Examiner—Thurman K. Page
Assistant Examiner—Leon R. Horne
Attorney, Agent, or Firm—Wegner, Cantor, Mueller & Player

[57] ABSTRACT

The agents for the treatment of conditions of severe pain, and especially of tumor pain and post-operative pain, consist of soft gelatin capsules containing from about 30 to about 50 parts by weight of ibuprofen and from about 1.5 to about 4 parts by weight of codeine and/or physiologically compatible salts thereof, partially dissolved and partially suspended in about 68.5 to about 46 parts by weight of polyoxyethylene-polyoxypropylene-diol or in a mixture comprising about 30 to about 76 parts by weight of polyoxyethylene-polyoxypropylene- diol or polyethylene-glycol or polypropyleneglycol and from about 7 to about 40 parts by weight of a physiologically compatible surfactant.

12 Claims, 8 Drawing Sheets

CODEINE PLASMA LEVEL:
- ●——● IBUPROFEN-CODEINE DRAGÉES
- ×--× IBUPROFEN-CODEINE CAPSULES (INVENTION)

FIG. 7b

IBUPROFEN PLASMA LEVEL:
- ●——● IBUPROFEN-CODEINE DRAGÉES
- ×--× IBUPROFEN-CODEINE CAPSULES (INVENTION)

AGENTS FOR THE TREATMENT OF SEVERE PAIN AND PREPARATION OF SAID AGENTS

BACKGROUND AND SUMMARY OF THE INVENTION

The present invention relates to agents for the treatment of conditions of severe pain, especially tumor pain and postoperative pain, and to a process for preparing said agents.

From the EP-A-0 178 436 (Application No. 85 111 013.0) there have been known soft gelatin capsules containing ibuprofen and processes for preparing same. Said soft gelatin capsules have proven to be useful for alleviating acute pain with a rapid onset of action, since they rapidly release the active ingredient ibuprofen and, hence, create a good bioavailability of the active substance.

Cooper et al. investigated the analgetic activity of combinations of ibuprofen and codeine and determined that codeine increases the analgetic activity of ibuprofen somewhat; however, this increase was so small that it has not been considered to be of sufficient statistical significance; cf. Pharmacotherapy 1982; 2:162-167.

Abraham Sunshine et al. quote investigations on the alleviation of pain upon extraction of the rear molars (Giles and Pickvance; Frame et al.) and after episiotomy (Norman et al.). Also here it was found that the simultaneous administration of ibuprofen and codeine, although it is more effective than that of ibuprofen alone, did not reveal any statistically significant differences. According to investigations by Abraham Sunshine et al. themselves, upon episiotomy (incision for facilitating birth) only the high dose of ibuprofen plus codeine (400 mg + 60 mg) exhibited an analgetic activity improved over that of ibuprofen alone. Lower doses of the combination were not better than ibuprofen (Clin. Pharm. Ther. 1987; 42: 374-380).

Thus, ibuprofen is a well tolerated and an effective analgesic which, however, is only employed against lighter and/or acute pain. For the treatment of conditions of severe pain, and especially of tumor pain and postoperative pain, it is still necessary to apply morphine or morphine derivatives. Morphine and morphine derivatives are known to cause a rapid addiction and, thus, should only be used if all remaining analgesics failed to be effective.

Therefore, it is the object of the present invention to develop an agent for the treatment of conditions of severe pain, and especially of tumor pain and post-operative pain, which does not include morphine or any morphine derivative. Surprisingly, said object can be attained by agents consisting of soft gelatin capsules containing from 30 to 50 parts by weight of ibuprofen and from 1.5 to 4 parts by weight of codeine and/or physiologically compatible salts thereof, partially dissolved and partially suspended in about 68.5 to 46 parts by weight of polyoxyethylene-polyoxypropylene-diol or in a mixture comprising about 30 to 76 parts by weight of polyoxyethylene-polyoxypropylene-diol or polyethylene-glycol or polypropyleneglycol and from about 5 to 40 parts by weight of a physiologically compatible surfactant.

A comparison to dragées containing the same amounts of ibuprofen and codeine confirmed the results reported by Cooper et al. and Sunshine et al. and has shown that such a combination is not suitable for treating severe pain conditions, and more specifically tumor pain or postoperative pain. In contrast thereto, the agent according to the invention exhibits a surprisingly good effect in many patients, comprising a very rapid onset of action on the one hand, and a relatively long duration of the action on the other hand, so that a subsequent administration must follow only relatively late. Thus, it has been found that in a great many cases the administration of morphine and/or morphine derivatives can be avoided or that such agents will be used at a substantially later stage.

Thus, the soft gelatin capsules according to the invention generally contain, in addition to the partially dissolved and partially suspended ibuprofen, the same solvents as the soft gelatin capsules of EP-A-0 178 436 (Application No. 85 111 013.0). Thus, preferably, they also contain up to 3 parts by weight of 1,2-propyleneglycol. They preferably contain polyoxyethylene-glycerol-tri-hydroxystearate, polyoxyethylene-($C_{12-18}$)-fatty alcohol ether, polyoxyethylene-stearate, polyoxyethylene-sorbitan-mono-($C_{12-18}$)-fatty acid ester, polyoxyethylene- polyoxypropylene-diol or mixtures thereof as a surfactant.

The preparation of the agents according to the invention is also carried out in a manner similar to the preparation of soft gelatin capsules containing ibuprofen, namely in a manner such that from 15 to 30 parts by weight of ibuprofen ar dissolved in 70 to 85 parts by weight of polyoxyethylene-polyoxypropylene-diol or in a mixture comprising 30 to 76 parts by weight of polyoxyethylene-polyoxypropylene-diol or polyethyleneglycol or polypropyleneglycol and 7 to 40 parts by weight of a physiologically compatible surfactant at temperatures of between 45° C. and 65° C., allowed to cool to room temperature, in addition up to 40 parts by weight of ibuprofen and 1.5 to 4 parts by weight of codeine and/or its physiologically compatible salts are suspended in the solution after cooling, and the mixture is incorporated in soft gelatin capsules in a per se known manner.

Particularly preferred are agents which contain from 40 to 45 parts by weight of ibuprofen and from 2.5 to 3 parts by weight of codeine phosphate . 0.5 $H_2O$, which in part have been dissolved and in part have been suspended in a mixture comprising ±rom about 86 to 90 parts by weight of polyoxyethylene-polyoxypropylene-diol, about 8 to 12 parts by weight of polyoxyethylene(40)-glycerol-tri-hydroxystearate and from about 1.5 to 2.5 parts by weight of 1,2-propyleneglycol.

They are prepared by first dissolving 20 to 25 parts by weight of ibuprofen in a warm mixture of from 86 to 90 parts by weight of polyoxyethylene-polyoxypropylene-diol, 8 to 12 parts by weight of polyoxyethylene(40)-glycerol-tri-hydroxystearate and from 1.5 to 2.5 parts by weight of 1,2-propyleneglycol, then allowing the obtained mixture to cool down to room temperature, and suspending in said mixture further 20 to 25 parts by weight of ibuprofen and 2.5 to 3 parts by weight of codeine phosphate . 0.5 $H_2O$, and then filling the resultant mixture into soft gelatin capsules.

These agents have been proven to be particularly valuable because they contain an especially high amount of active ingredients per weight and volume unit of the soft gelatin capsule and, nevertheless provide the active substances fast and at a high bioavailability. Thus, the capsule size or the number of capsules to be taken are within a range which is as low as possible.

BRIEF DESCRIPTION OF THE DRAWINGS

FIGS. 8a–8c show the assessment of pain of the inventive capsules (shaded bars) in comparison with capsules according to EP 178,436 (white bars).

In the subsequent Examples there are described the preparation of a preferred formulation and the comparative tests with dragées containing the same amount of active substance as the soft gelatin capsules according to the invention.

EXAMPLE 1

A mixture comprising 196.65 g of Polyoxyethylene-polyoxypropylene-diol 1900 {Pluronic ® L 35, Wyandotte Chemicals Corp}, 21.60 g of Polyoxyethylene(4?)-glycerol trihydroxystearate (Cremophor ® RH 40, BASF) and 4.50 g of 1,2-propyleneglycol is prepared by stirring at from 60° C. to 70° C.; the resultant mixture is cooled to 50° C., and 90.00 g of ibuprofen are portion-wise added thereto with stirring. In the resultant solution there are suspended at from 15° C. to 20° C. another 90.00 g of finely divided ibuprofen and 11.25 g of codeine phosphate 0.5 $H_2O$. The suspension thus obtained is incorporated in soft gelatin capsules of suitable size. 0.920 g of the suspension contain 400 mg of ibuprofen and 25 mg of codeine phosphate . 0.5 $H_2O$.

EXAMPLE 2

The soft gelatin capsules prepared according to Example 1 were tested in a comparative study in altogether 20 patients suffering from pain conditions such as tumor pain, that is in comparison to ibuprofen-codeine dragées containing the same amount of the active ingredient.

The diagnoses included mammary carcinoma, bronchial and lung-basal carcinoma with bone metastasis, oesophageal and tongue-basal carcinoma with lymph metastasis, colon carcinoma with liver metastasis, plasma-cytoma with compression fracture, sigmoid carcinoma and others.

From the calendar dates on the first, second and third days of treatment, the duration of treatment in days after the second and third days of examination was calculated by means of a program, and by means of another program the time of when to administer a booster dose (repetition of administration) was calculated in hours relative to the first administration on the same date of examination.

Statistics were determined for the metric parameters describing the patient and the tests as well as for the minimum time of action, the duration of the action, the two ordinal pain parameters (intensity of and ease of pain), the ranks of the latest onset of action and of the latest loss of action, and the assessments of affectivity and of compatibility.

Four-area-tests according to FISHER (Statistische Methoden für die Wissenschaft, London: Oliver-Boyd; 1956) were employed for the binary parameters describing the patients and the side-effects encountered upon application in accordance with the regimen. The comparison of groups with respect to the metric patient-describing and test-describing parameters was made by means of the U-TEST according to Mann-Whitney Ann. Math. Stat. 1947: 18: 50–60). For the random-critical comparison of the two groups of patients over the three days of examination, simultaneous U-tests with alpha-adjustment (Buck, EDV in Medizin und Biologie 1976, 7; 65–75) were employed for the dosage rate, intensity of pain, easing of pain, the ranks of the latest onset of action and of the latest loss of action, and the assessments of affectivity and of compatibility by the testing physician.

The differences in the effectiveness determined between the two groups of patients are statistically significant. The results are summarized and represented by the graphs of FIGS. 1 through 5.

EXAMPLE 3

Figure 1A:
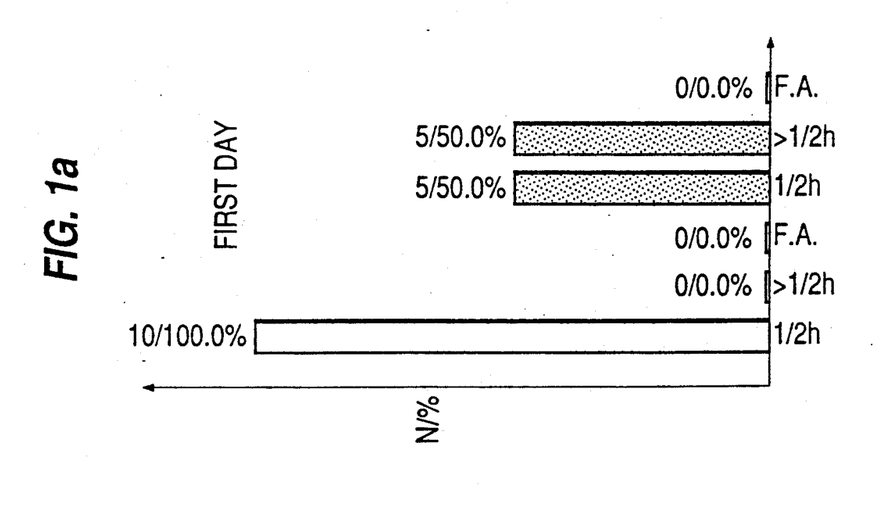
FIGS. 1a–1c show the onset of action after the first intake (N/%) of ibuprofen-codeine capsules according to the invention (white bars) in comparison with dragees (shaded bars), the first, second and third days after intake, respectively. In these figures, ½ h symbolizes the onset of action within ½ hour after intake, >½ h stands for the onset of action ½ hour after intake, and F.A. means that no indications are available.
Figure 1B:
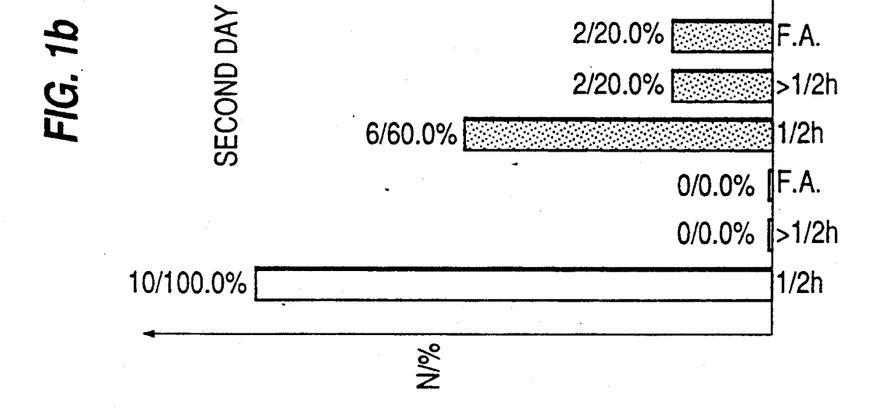
Figure 1C:
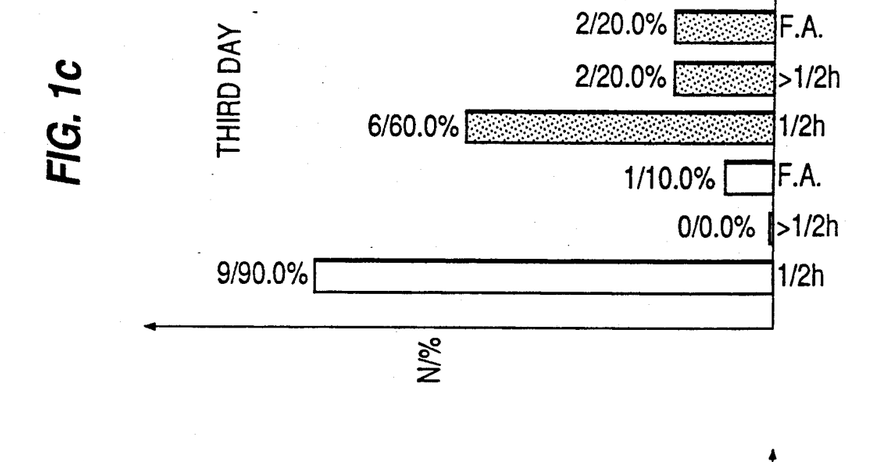
Figure 2A:
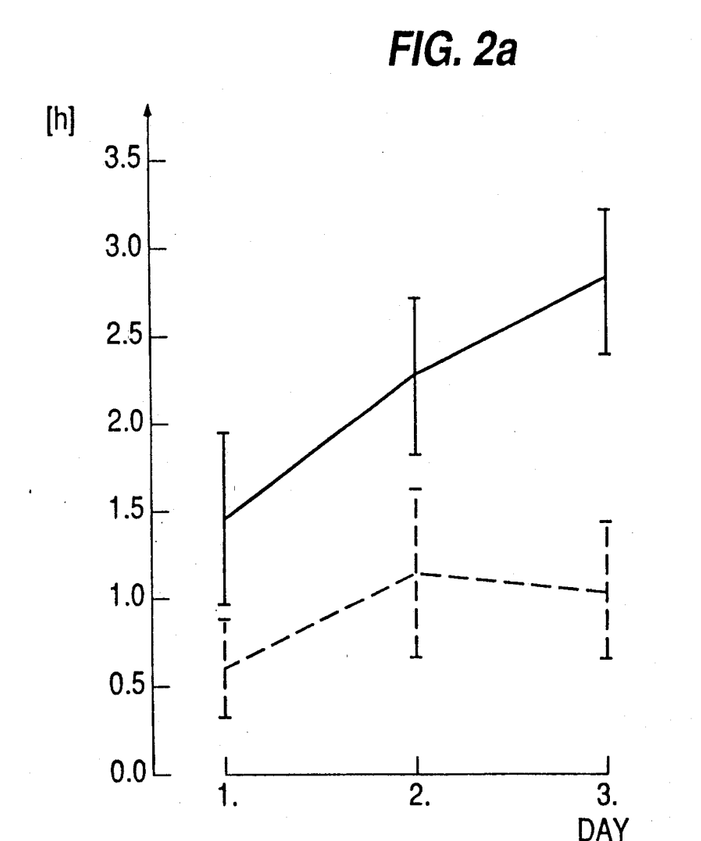
FIGS. 2a and 2b show the minimum time, in hours, within which patients were free from pain after the first intake (FIG. 2a) and repetition of administration (FIG. 2b) of the ibuprofen-codeine capsules of the invention (shown by the solid lines) compared with dragees (represented by dashed lines).
Figure 2B:
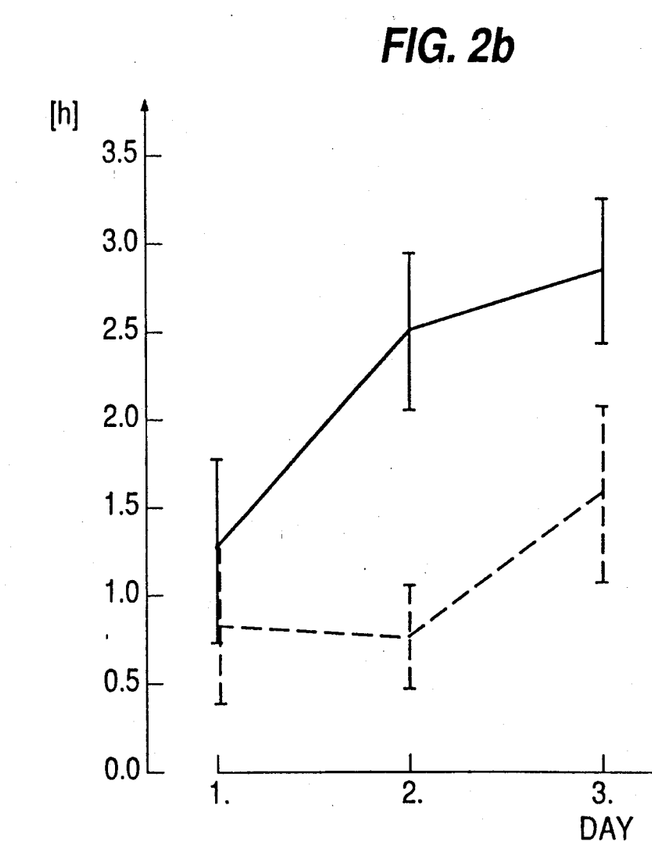
Figure 3:
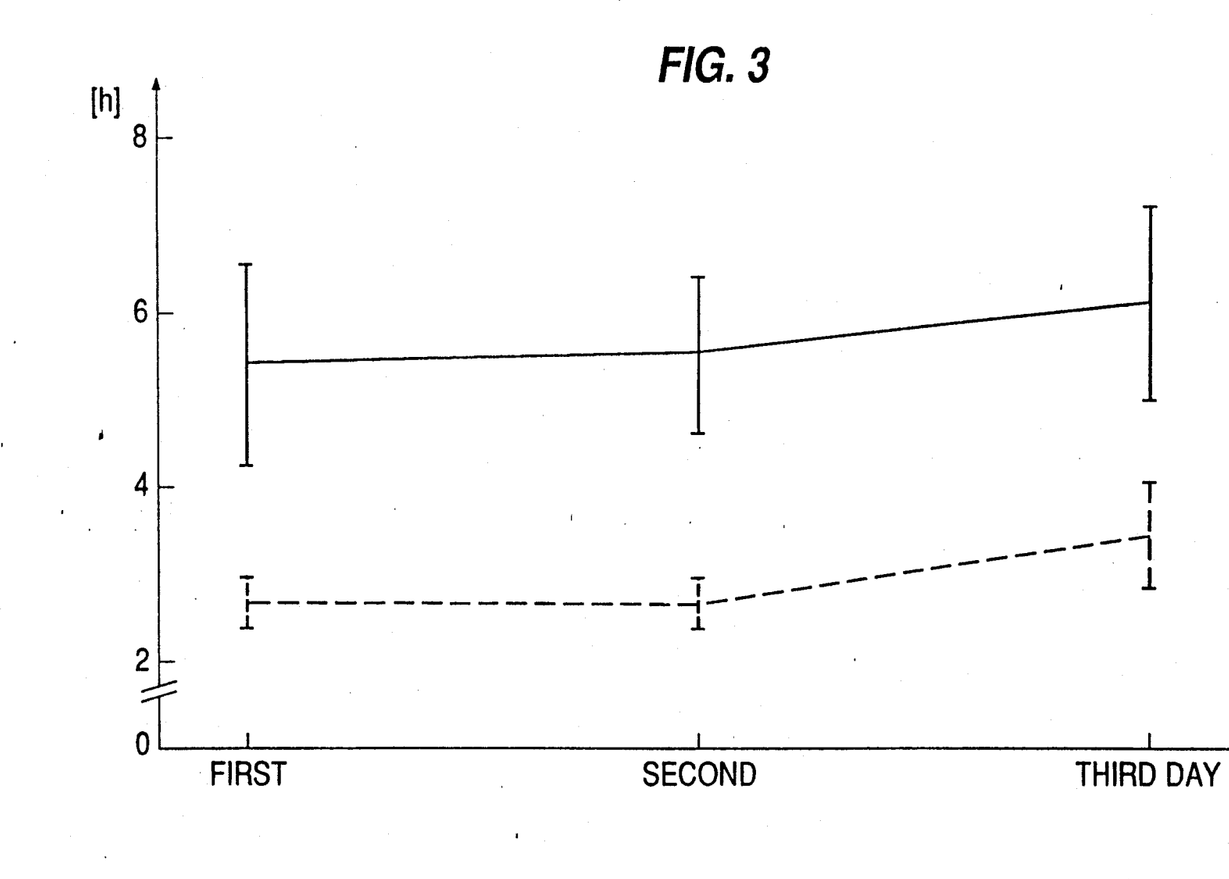
FIG. 3 shows the duration of action, in hours, of the ibuprofen-codeine capsules (solid line) and dragees (dashed line).
Figure 4A:
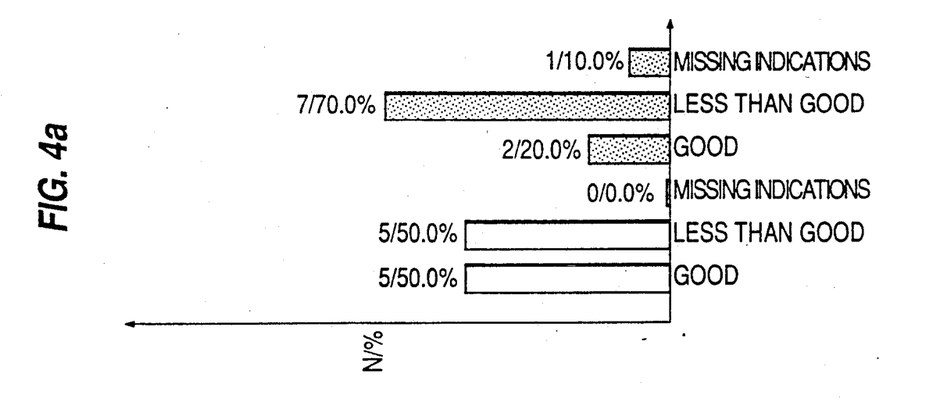
FIGS. 4a–4c respectively show the assessment of effectivity (N/%) by the testing physician the first, second and third days of ibuprofen-codeine capsules (white bars) compared with dragees (shaded bars). In these figures, "Less than good" means satisfactory, moderate or poor.
Figure 4B:
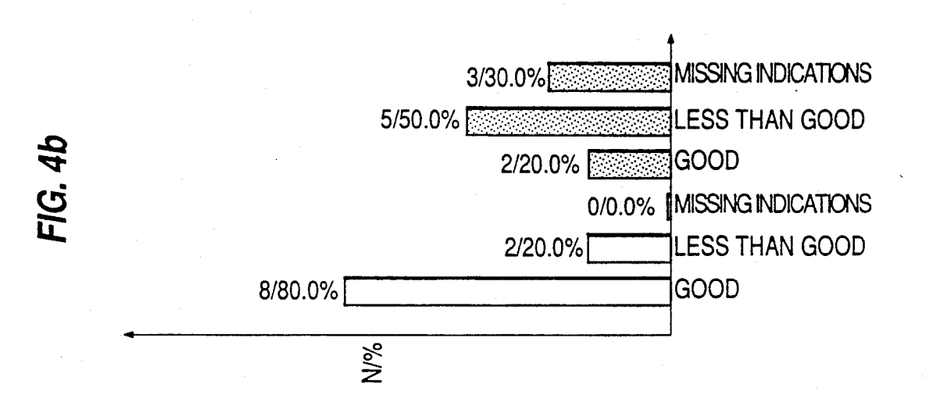
Figure 4C:
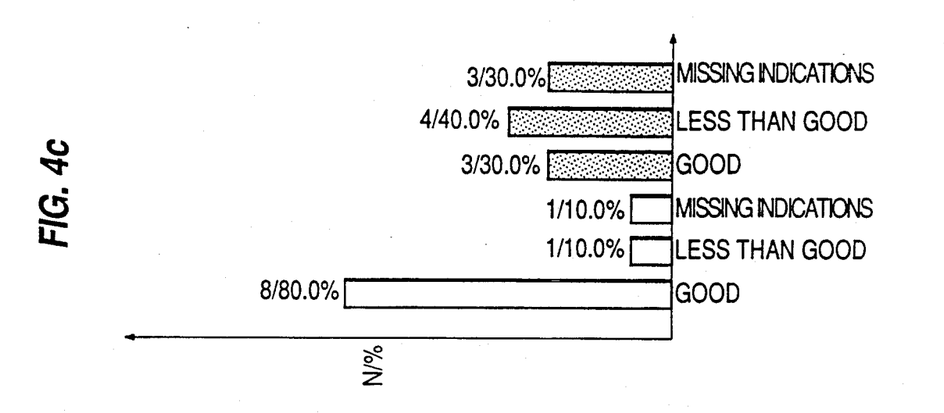
Figure 5A:
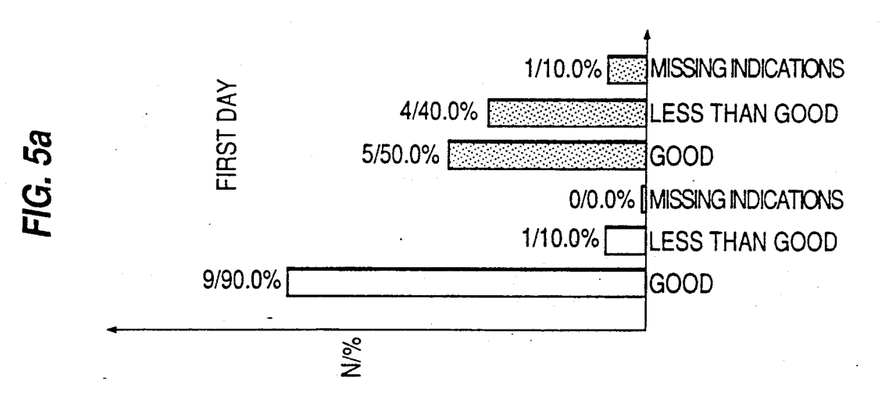
FIGS. 5a–5c show for the first day, second day and third day, respectively, the assessment of compatibility by the testing doctor of ibuprofen-codeine capsules (white bars) and dragees (shaded bars), with "Less than good" indicating satisfactory, moderate or poor.
Figure 5B:
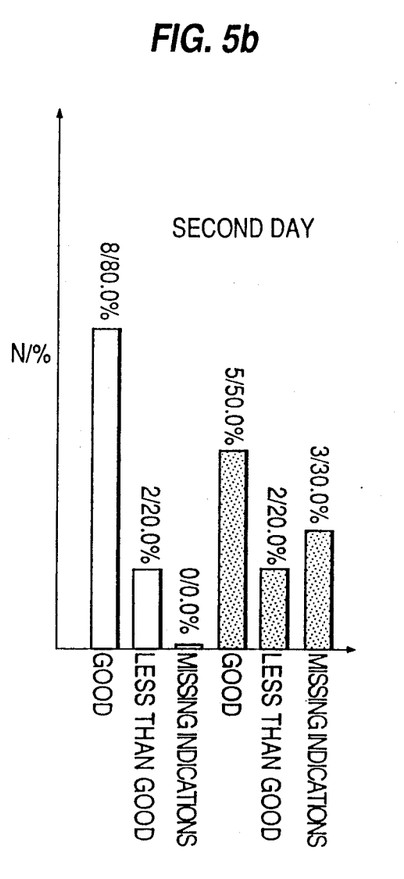
Figure 5C:
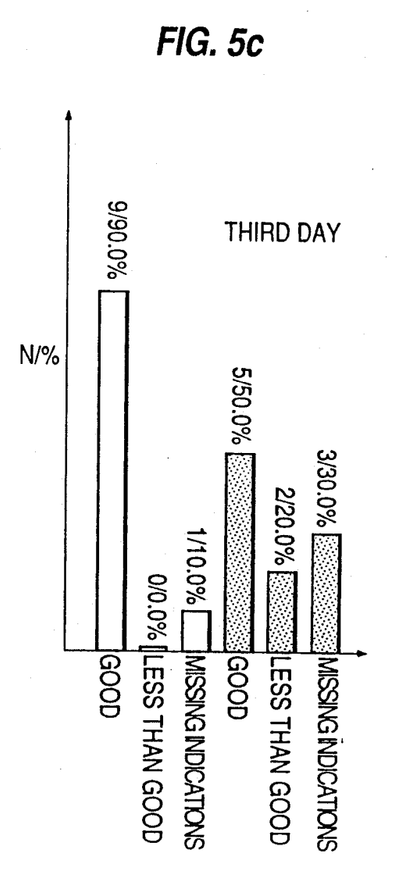
Figure 6:
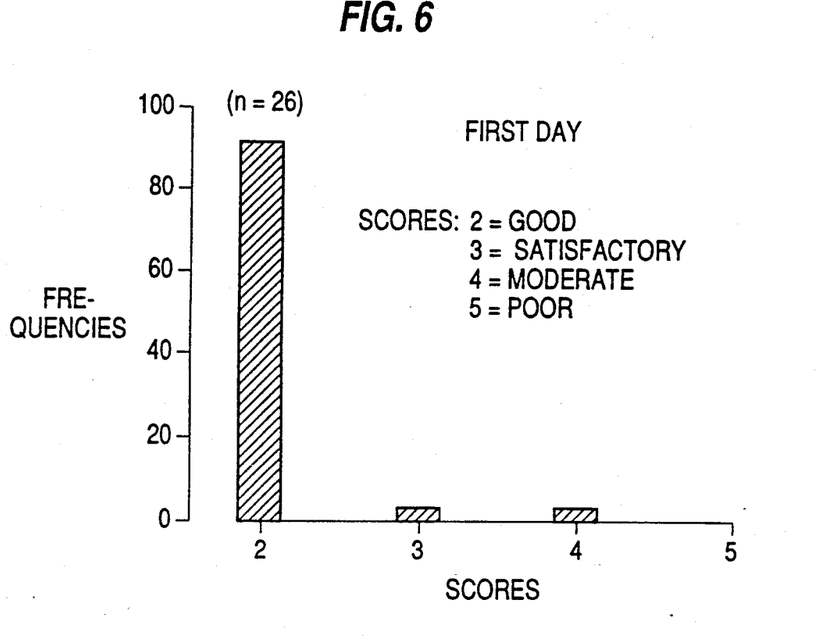
FIG. 6 summarizes data from an open study of activity of the inventive ibuprofen-codeine capsules in patients suffering from conditions of severe post-operative pain.

The soft gelatin capsules prepared according to Example 1 were tested in an open study of the effectiveness with 26 patients suffering from conditions of heavy postoperative pain. The indications for surgery were as follows:

Gonarthrosis
˜ Necrosis at the foot after ankle joint fracture
Metal removal from the ankle joint
Endoprosthesis
Knee endoprosthesis
Hammer-toe
Chiseling off an exostosis
Meniscotomy
Arthrodesis surgery, ankle joint Radius fracture
Bursitis knee joint extirpation
Ulnar joint revision The patients were administered with 3 times one capsule per day. The effect lasted for from three to 10 hours, 5.35 hours on the average. The results are shown in Tables 1 and 3 and in FIG. 6.

TABLE 1

Assessment of Pain on the First Day (n = 26)
Score Evaluation: 0 = Non-existent
1 = Light
2 = Moderate
3 = Strong
4 = Very strong
m.v. = Missing Values

| Scores | 0 | 1 | 2 | 3 | 4 | m.v. |
|---|---|---|---|---|---|---|
| Pain before therapy | 0 | 0 | 1 | 24 | 0 | 1 |
| Pain after ½ hour | 4 | 15 | 4 | 2 | 0 | 1 |
| Pain after 1 hour | 7 | 14 | 2 | 2 | 0 | 1 |
| Pain after 2 hours | 8 | 12 | 3 | 2 | 0 | 1 |
| Pain after 3 hours | 8 | 10 | 5 | 2 | 0 | 1 |
| Pain after 4 hours | 7 | 11 | 5 | 1 | 0 | 2 |

TABLE 2

Ease of Pain [Ease] on the First Day (n = 26)
Score Evaluation: 1 = Complete
2 = Distinct
3 = Low
4 = Not at all
m.v. = Missing Values

| Scores | 1 | 2 | 3 | 4 | m.v. |
|---|---|---|---|---|---|
| Ease after ½ hour | 4 | 16 | 4 | 2 | 0 |
| Ease after 1 hour | 7 | 15 | 2 | 2 | 0 |
| Ease after 2 hours | 8 | 14 | 2 | 2 | 0 |
| Ease after 3 hours | 8 | 9 | 7 | 2 | 0 |
| Ease after 4 hours | 7 | 12 | 5 | 1 | 1 |

EXAMPLE 4

Further tests with humans were carried out in order to determine in what way ibuprofen and codeine act when formulated according to the invention.

From the Experimental Report, Part A, it will be seen that surfactants do not change the availability of each active substance in the same way. Upon the administration of the capsules of the invention, the codeine plasma level was reduced to about one half of its initial value after about two hours, whereas this happened to the dragées after about 4 hours. The plasma level of the ibuprofen from the capsule of the invention takes a similar course, whereas the dragée produces a flatter curve of the ibuprofen plasma level, so that here the plasma level decreased to about one half of its initial value not sooner than after about 4½ hours. It is noteworthy that the plasma level of the two compounds according to the invention is synchronized, whereas for the dragée it is observed in the beginning that the curves are poorly congruent. As is evident from the plasma level curves and from the $c_{max}$ values, for ibuprofen in the initial phase the availability from the capsules is improved over that from the dragées. On the other hand, the AUC values tell that the bioavailability of ibuprofen over the period of observation is equal within the limits of error for both preparations. For codeine, the plasma level curves as well as the AUC and $c_{max}$ values as determined do not show any difference with respect to the bioavailability. The somewhat higher codeine AUC value of the dragées even points to a better availability. However, the difference between the AUC values of the two forms is not statistically significant.

It is true, in the case of the capsule according to the invention, the resorption of the ibuprofen, as compared to the dragée, is accelerated in the initial phase immediately after intake; however, the availability of the codeine is not influenced. The slower decrease of the dragée plasma level curves as compared to those of the capsules would even raise the expectation of an improved effectiveness and, above all, a longer duration of the action of the dragées as compared to that of the capsules. However, surprisingly, the findings of the Example 2 according to the invention produced just the opposite result, namely a better and longer-lasting pain alleviation after the application of the capsules of the invention. These results show that in the case of the combination of ibuprofen and codeine in the capsules according to the invention, the surprisingly good effect of the alleviation of pain cannot be attributed alone to the addition of surfactants. Here, obviously some unexpected metabolic and synergistic effects are involved between active and inactive substances.

Part B of Experimental Report shows another advantage associated with the use of the capsules according to the invention. Cooper et al. (Pharmacotherapy, 1982, 2, 162-167) observed that the combination of 400 mg of ibuprofen + 60 mg of codeine exhibits an analgetic effect which is slightly, though not statistically significantly, improved over that provided by 400 mg of ibuprofen alone. According to Sunshine et al., loc. cit., for pain alleviation only a high dose of 400 mg of ibuprofen and 60 mg of codeine is superior to the single dose of 400 mg of ibuprofen. Low doses of codeine (30 mg) and ibuprofen did not show an improvement over ibuprofen alone. However, if the combination of the active substances is administered in the form of the capsules according to the invention, then already the low additive amount of 25 mg of codeine causes a statistically significant better analgetic effect than is produced by ibuprofen alone. Also this finding unambiguously shows that surprising effects occur upon the administration of the capsule according to the invention.

PART A

Comparison of the bioavailabilities of the active substances from ibuprofen-codeine capsules (Invention, Example and ibuprofen-codeine dragées.

Figure 7A:
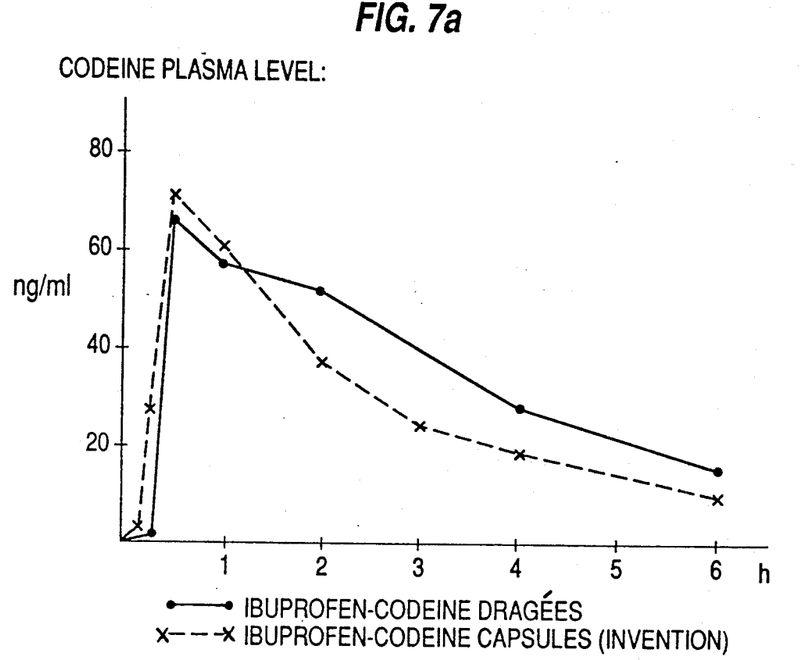
FIGS. 7a and 7b show the bioavailability of codeine and ibuprofen, respectively for capsules of the invention and dragees.
Figure 7B:
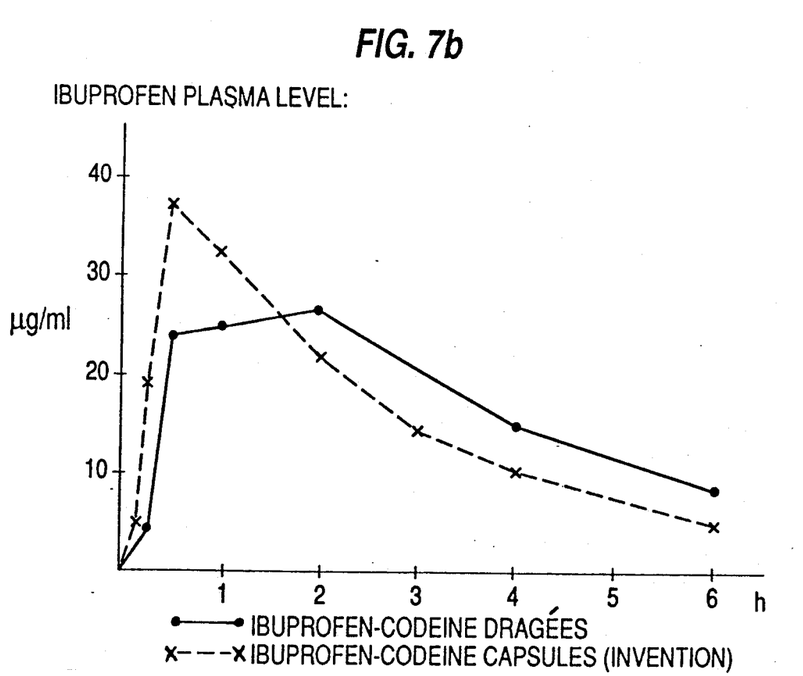

The study was designed as an open experiment. The capsules or dragées used each contained 400 mg of ibuprofen + 25 mg of codeine phosphate. A total of 14 healthy male volunteers participated in the study (6 for the dragées and 8 for the capsules). The test persons were each administered with one of the preparations; then blood was taken from test persons after definite periods of time, and the ibuprofen and codeine contents were determined in the blood samples. The average values obtained from these plasma assays are graphically shown vs. time in the FIG. 7. From these curves of the average values, the parameters relevant to the assessment of the bioavailability were calculated: AUC = area under the plasma level curve as a measure for the amount of substance present in the organism over the observation period, and $c_{max}$ = maximum plasma concentration of the active substances. The calculations were done with the use of a Commodore cbm 3032, those of AUC by means of the trapezoid rule.

| Capsules (invention) | Dragées: |
| --- | --- |
| Ibuprofen: | Ibuprofen: |
| AUC = 98.5 h.μg/ml | AUC = 106.5 h.μg/ml |
| $c_{max}$ = 35.9 μg/ml | $c_{max}$ = 27.9 μg/ml |
| Codeine: | Codeine: |
| AUC = 180.9 h.ng/ml | AUC = 217.2 h.ng/ml |
| $c_{max}$ = 70.8 ng/ml | $c_{max}$ = 68.7 ng/ml |

The results are summarized in FIG. 7.

PART B

Comparison of the effectiveness of the ibuprofen-codeine capsules according to the invention, Example 1, with that of ibuprofen capsules according to EP-A-178 436 (Example 19).

Figure 8A:
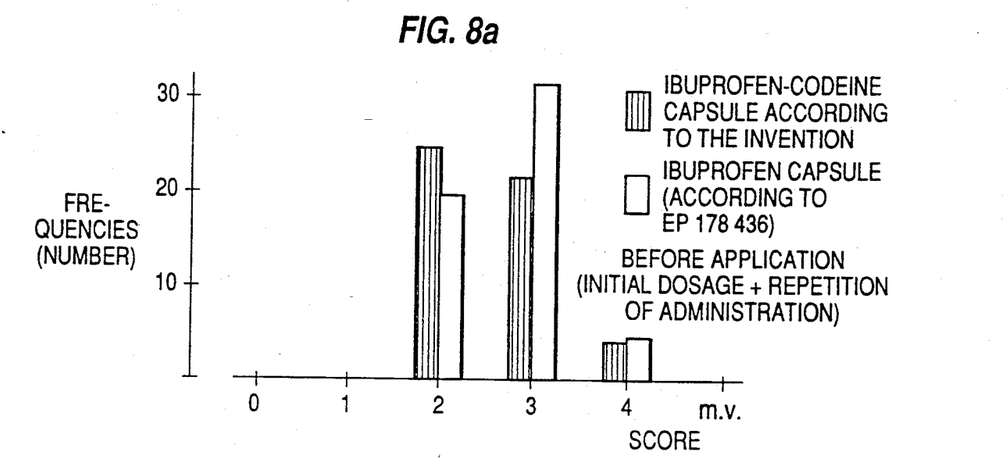
FIG. 8a is a bar graph showing the scores before application (initial dosage and repetition of administration)
Figure 8B:
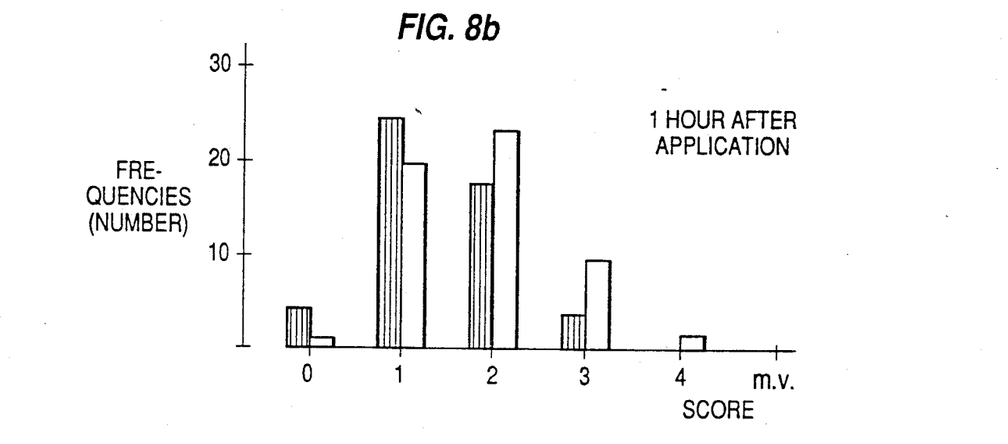
FIG. 8b is a bar graph showing the scores one hour after application.
Figure 8C:
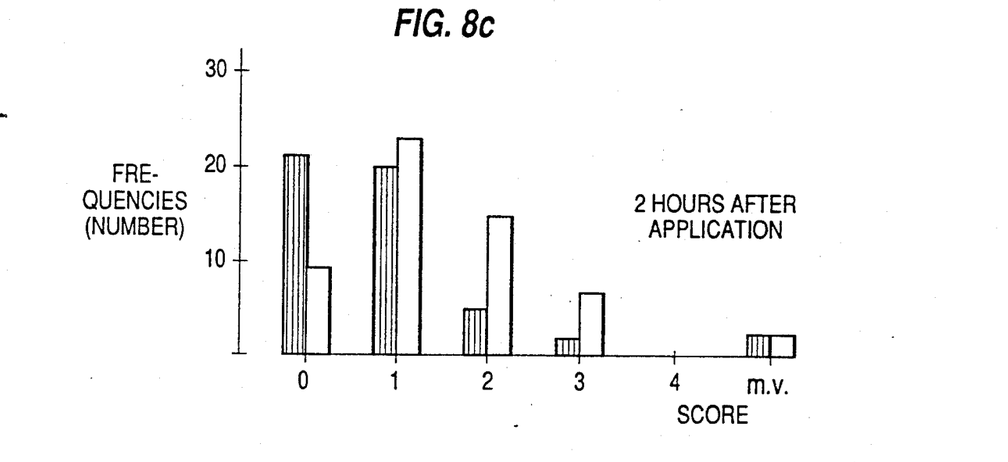
FIG. 8c is a bar graph showing the scores two hours after application.
Figure 9:
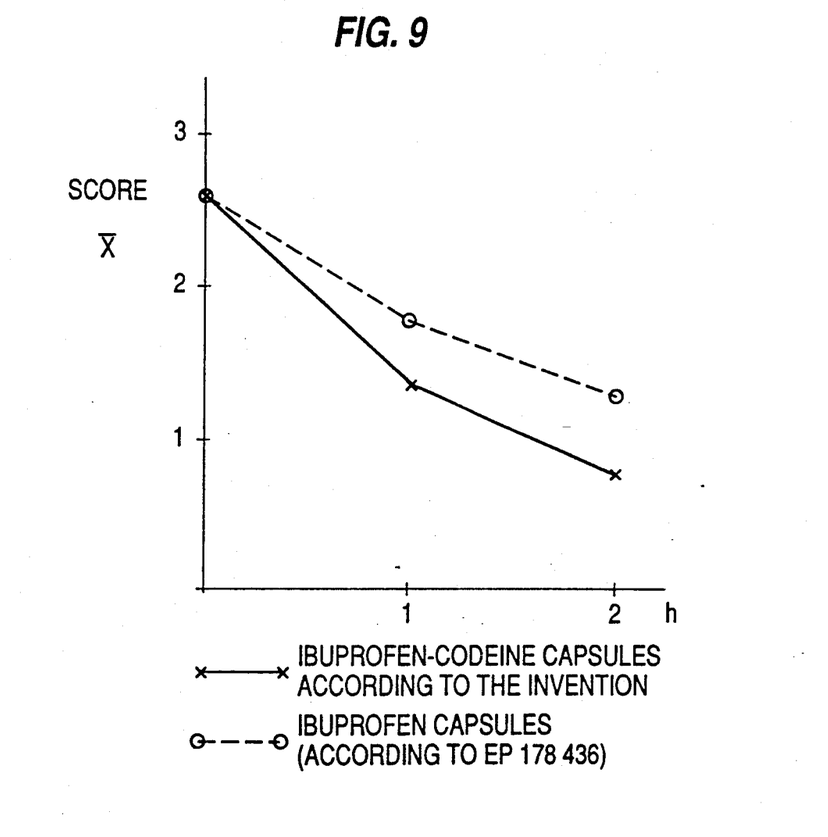
FIG. 9 is a graph showing the assessment of pain using ibuprofen-codeine capsules according to the invention and ibuprofen capsules according to EP 178,436.

The study was designed as an open cross-over experiment with randomized assignment of the preparations. The capsules according to the invention used in the examination contained 400 mg of ibuprofen + 25 mg of codeine phosphate, while the capsules according to the EP-A-178 436 contained 400 mg of ibuprofen. A total of 16 patients suffering from humeroscapular periarthritis, lumbago or cervical spinal column syndrome or arm-shoulder syndrome, respectively, participated in the study. On the day of the test, one capsule was initially administered, and then, after the action had worn off, one capsule each was subsequently administered. In this manner, two to four times one capsule, after intervals of from 3 to 6 hours, were taken within the test period of 12 hours. In each case inquiries on the pain conditions were made immediately before, and one hour and two hours after the application FIG. 8); the answers were rated by the following standard:

0 = Non-existent
1 = Light
2 = Moderate
3 = Strong
4 = Very strong
m.v. = Missing Value From the individual scores for each patient there were formed the average values (pain intensity; Table 3). Finally, the effectiveness integrals (areas under the score vs. time curves), representing a measure for the pain intensity over the observation period, were calculated by means of the trapezium [trapezoid] rule. The effectiveness integrals were calculated with a Commodore cbm 3032. The difference between the average effectiveness integrals ($\bar{x}$) of t he ibuprofen-codeine capsules and the ibuprofen capsules is significant (one-sided U test according to Wilcoxon, Mann and Whitney; FIG. 9). Moreover, from the number of repetitions there may be drawn conclusions with respect to an extend®d period of action of the ibuprofen-codeine capsules as compared to the ibuprofen capsules (Table 3).

The results of the instant study clearly show that the ibuprofen-codeine capsules according to the invention are superior to the previously known ibuprofen capsules according to EP-A-178 436 with respect to pain assessment, influence on pain intensity and duration of action.

TABLE 3

| | Assessment of Pain | | | | | |
| --- | --- | --- | --- | --- | --- | --- |
| | Ibuprofen-codeine capsule according to the invention | | | Ibuprofen capsule (as of EP 178 436) | | |
| Patient (Initial Letters) | Pain intensity (Average score) after 0 | 1 | 2 h | Integral of action (h.score) | Pain intensity (Average score) after 0 | 1 | 2 h | Integral of action (h.score) |
| 1 (HM) | 3 | 1,7 | 1 | 3,7 | 3 | 1 | 1 | 3,0 |
| 2 (TK) | 2 | 1,7 | 1 | 3,2 | 2 | 1,3 | 1,3 | 2,9 |
| 3 (CH) | 2,8 | 0,7 | 0 | 2,1 | 2,8 | 2,7 | 1,7 | 5,0 |
| 4 (PA) | 3 | 1,3 | 1,3 | 3,4 | 3 | 2 | 2 | 4,5 |
| 5 (NE) | 2 | 0,7 | 0 | 1,7 | 2 | 1,5 | 1,3 | 3,2 |
| 6 (BM) | 3 | 2 | 2,2 | 4,6 | 3 | 2 | 1,5 | 4,3 |
| 7 (PT) | 2,5 | 1 | 0 | 2,2 | 2,5 | 0,7 | 0,5 | 2,2 |
| 8 (HT) | 2,5 | 0,7 | 0 | 1,9 | 2,5 | 1,7 | 0,7 | 3,3 |
| 9 (AN) | 3,4 | 1,7 | 1,3 | 4,0 | 3,4 | 3,2 | 2,7 | 6,2 |
| 10 (PB) | 2,5 | 1 | 0,7 | 2,6 | 2,5 | 1,7 | 1 | 3,5 |
| 11 (AT) | 2,6 | 1,5 | 0,7 | 3,1 | 2,6 | 1,7 | 1 | 3,5 |
| 12 (HS) | 2 | 1 | 0 | 2,0 | 2 | 1,7 | 1 | 3,2 |
| 13 (KC) | 2,3 | 2 | 1 | 3,6 | 2,3 | 2 | 2 | 4,2 |
| 14 (DA) | 3,7 | 2,7 | 2 | 5,5 | 3,7 | 3 | 3 | 6,4 |
| 15 (JB) | 2,3 | 1,7 | 0,3 | 3,0 | 2,3 | 2 | 0 | 3,1 |
| 16 (AH) | 2,5 | 1,3 | 0,5 | 2,8 | 2,5 | 1 | 0 | 2,3 |
| $\bar{x}$ | 2,6 | 1,4 | 0,8 | 3,1 | 2,6 | 1,8 | 1,3 | 3,8 |
| Number of dosage repetitions | 35 | | | | 41 | | | |

What is claimed is:

1. A pharmaceutical dosage unit for the treatment of severe pain which is a soft gelatin capsule which includes:
   pain relief ingredients comprising from about 30 to about 50 parts by weight ibuprofen and from about 1.5 to about 4 parts by weight codeine or a physiologically compatible salt thereof;
   at least one ingredient for partially dissolving and suspending said pain relief ingredients comprising (i) from about 68.5 to about 46 parts by weight of polyoxyethylene-polyoxypropylene-diol or (ii) from about 30 to about 76 parts by weight polyoxyethylene-polyoxypropylene-diol, polyethyleneglycol or polypropylene glycol, said pain relief ingredients being partially dissolved and partially suspended in said at least one ingredient; and
   from about 5 to about 40 parts by weight of a physiologically compatible surfactant selected from the group consisting of polyoxyethylene-glycerol-trihydroxystearate, polyoxyethylene-($C_{12-18}$)-fatty alcohol ether, polyoxyethylene-stearate, polyoxyethylene-sorbitan-mono-($C_{12-18}$)-fatty acid ester, polyoxyethylene-polyoxypropylene-diol and mixtures thereof.

2. The dosage unit according to claim 1, which comprises up to 3 parts by weight of 1,2-propyleneglycol.

3. The dosage unit according to claim 2, characterized in that it comprises polyoxyethylene-glycerol-trihydroxystearate, polyoxyethylene-($C_{12-18}$)-fatty alcohol ether, polyoxyethylene-stearate, polyoxyethylene-sorbitan-mono($C_{12-18}$)-fatty acid ester, polyoxyethylene-polyoxypropylene-diol or mixtures thereof as a surfactant.

4. The dosage unit according to claim 1, characterized in that it comprises from about 40 to 45 parts by weight of ibuprofen and from about 2.5 to about 3 parts by weight of codeine phosphate . 0.5 $H_2O$, which in part have been dissolved and in part have been suspended in a mixture comprising from about 86 to about 90 parts by weight of polyoxyethylene-polyoxypropylene-diol, about 8 to 12 parts by weight of polyoxyethylene(40)-glycerol-tri-hydroxystearate and from about 1.5 to about 2.5 parts by weight of 1,2-propyleneglycol.

5. The dosage unit according to claim 2, characterized in that it comprises from about 40 to about 45 parts by weight of ibuprofen and from about 2.5 to about 3 parts by weight of codeine phosphate . 0.5 $H_2O$, which in part have been dissolved and in part have been suspended in a mixture comprising from about 86 to about 90 parts by weight of polyoxyethylene-polyoxypropylene-diol, about 8 to 12 parts by weight of polyoxyethylene(40)-glycerol-tri-hydroxystearate and from about 1.5 to about 2.5 parts by weight of 1,2-propyleneglycol.

6. The dosage unit according to claim 1, characterized in that it comprises from about 40 to about 45 parts by weight of ibuprofen and from about 2.5 to about 3 parts by weight of codeine phosphate . 0.5 $H_2O$, which in part have been dissolved and in part have been suspended in a mixture comprising from about 86 to about 90 parts by weight of polyoxyethylene-polyoxypropylene-diol, about 8 to about 12 parts by weight of polyoxyethylene(40)-glycerol-tri-hydroxystearate and from about 1.5 to about 2.5 parts by weight of 1,2-propyleneglycol.

7. A process for preparing a dosage unit for the treatment of severe pain, characterized in that from about 15 to about 20 parts by weight of ibuprofen are dissolved in about 70 to about 85 parts by weight of polyoxyethylene-polyoxypropylene-diol or i a mixture comprising about 30 to 76 parts by weight of polyoxyethylene-polyoxypropylene-diol or polyethylene-glycol or polypropyleneglycol and about 5 to about 40 parts by weight of a physiologically compatible surfactant selected from the group consisting of polyoxyethylene-glycerol-tri-hydroxystearate, polyoxyethylene-($C_{12-18}$)-fatty alcohol ether, polyoxyethylene-stearate, polyoxyethylene-sorbitan-mono-($C_{12-18}$)-fatty acid ester, polyoxyethylene-polyoxypropylene-diol and mixtures thereof at temperatures of between 45° C. and 65° C., allowed to cool to room temperature, in addition up to about 40 parts by weight of ibuprofen and about 1.5 to 4 parts by weight of codeine or its physiologically compatible salts or mixtures thereof are suspended in the solution after cooling, and the mixture is incorporated in soft gelatin capsules.

8. The process according to claim 7, characterized in that up to about 3 parts by weight of 1,2-propyleneglycol are added to the solvents.

9. The process according to claim 8, characterized in that polyoxyethylene-glycerol-tri-hydroxystearate, polyoxyethylene-($C_{12-18}$)-fatty alcohol ether, polyoxyethylene-stearate, polyoxyethylene-sorbitan-mono($C_{12-18}$)-fatty acid ester, polyoxyethylene-polyoxypropylene-diol or mixtures thereof are used as the surfactant.

10. The process according to claim 8, characterized in that first about 20 to 25 parts by weight of ibuprofen are dissolved in a warm mixture of from about 86 to about 90 parts by weight of polyoxyethylene- polyoxypropylene-diol, about 8 to 12 parts by weight of polyoxy- ethylene(40)-glycerol-tri-hydroxystearate and from about 1.5 to about 2.5 parts by weight of 1,2-propyleneglycol, then the resulting mixture is allowed to cool down to room temperature, and from about 20 to about 25 parts by weight of ibuprofen and from about 2.5 to about 3 parts by weight of codeine phosphate . 0.5 $H_2O$ are further suspended in said mixture, and then the resultant mixture is filled into soft gelatin capsules.

11. The dosage unit according to claim 1, wherein said surfactant is present in an amount form about 7 to about 40 parts by weight.

12. The dosage unit according to claim 1, wherein said surfactant is present in an amount of about 5 parts by weight.

* * * * *